United States Patent [19]

Lungu et al.

[11] Patent Number: 4,689,135
[45] Date of Patent: Aug. 25, 1987

[54] DEVICE FOR CONDITIONING A GAS SENSOR

[75] Inventors: Mihail Lungu, Reinfeld; Bernd Rogge, Scharbeutz, both of Fed. Rep. of Germany

[73] Assignee: Drägerwerk Aktiengesellschaft, Lübeck, Fed. Rep. of Germany

[21] Appl. No.: 833,357

[22] Filed: Feb. 25, 1986

[30] Foreign Application Priority Data

Feb. 26, 1985 [DE] Fed. Rep. of Germany ....... 3506688

[51] Int. Cl.⁴ .......................................... G01N 27/46
[52] U.S. Cl. .................................. 204/415; 204/279; 204/402; 73/1 G; 428/457
[58] Field of Search ............... 204/415, 1 K, 401, 279, 204/402; 73/1 G; 128/635; 428/195, 457

[56] References Cited

U.S. PATENT DOCUMENTS 3,824,157 7/1974 Macur ................................ 204/1 T

FOREIGN PATENT DOCUMENTS 2203942 8/1972 Fed. Rep. of Germany ...... 204/415
2836904 10/1979 Fed. Rep. of Germany ...... 204/415

Primary Examiner—T. Tung
Attorney, Agent, or Firm—Walter Ottesen

[57] ABSTRACT

A method is disclosed for conditioning a gas sensor. The electrode arrangement of the sensor is surrounded by an electrolyte and is partitioned off from the atmosphere by a gas-permeable membrane. The electrode arrangement is introduced into a calibrating gas and the calibrating gas is kept in isotonic equilibrium with the electrolyte. The composition of the electrolyte is not varied substantially while maintaining the operating conditions of the sensor and without having to introduce the sensor into a medium containing the calibrating gas. For this purpose, the membrane of the sensor is covered with a gas-tight and water-vapor-tight overlay, and the isotonic equilibrium is brought about and maintained by means of the gas that diffuses out of the electrolyte through the membrane as far as the overlay.

4 Claims, 1 Drawing Figure

U.S. Patent    Aug. 25, 1987    4,689,135
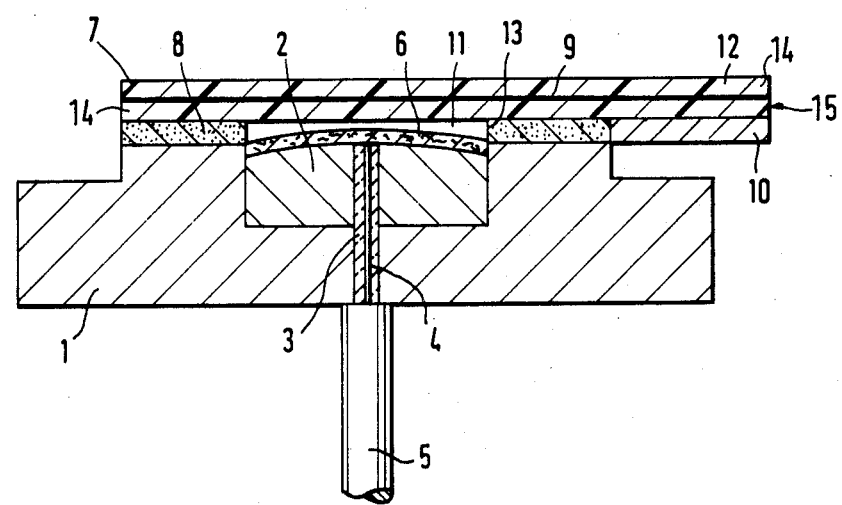

DEVICE FOR CONDITIONING A GAS SENSOR

FIELD OF THE INVENTION

The invention relates to a method for conditioning a gas sensor, in particular for measuring $CO_2$ partial pressure. The electrode array of the gas sensor is surrounded by an electrolyte and partitioned off from the atmosphere by a gas-permeable membrane and is introduced into a medium containing calibrating gas; the calibrating gas is held in isotonic equilibrium with the electrolyte. A device in the form of an overlay suitable for performing the method is also described.

BACKGROUND OF THE INVENTION

A method of this general type is described in German published patent application DE-OS No. 22 03 942.

In this publication, a sensor for measuring $CO_2$ partial pressure is described, the measurement-sensitive part of which comprises an electrode array which is surrounded by an electrolyte, which in turn is partitioned off from the ambient by a membrane that is permeable to $CO_2$ and water vapor. The electrode array measures the pH value of the electrolyte, which varies due to diffusion of $CO_2$ from the ambient atmosphere through the membrane into the electrolyte. If the sensor is exposed unprotected to the ambient atmosphere, which is the case while it is in storage, for instance, or during the intervals between two measurements, water vapor escapes into the ambient from the electrolyte through the membrane. If this type of sensor for measuring $CO_2$ partial pressure is kept at an elevated operating temperature, as is necessary for instance in transcutaneous measurement of the $CO_2$ partial pressure of the blood, then additional gaseous $CO_2$ diffuses out of an electrolyte, which contains carbonates in solution, into the ambient atmosphere. Because of the loss of water vapor and $CO_2$ from the electrolyte, the operating point of the sensor shifts because the electrolyte becomes alkaline due to the diffusion of $CO_2$ out of it thereby introducing a change in the pH value. The sensor is then operated outside the specified measurement range, which can falsify the indication and make the measurement results unusable.

Alkaline electrolytes are harmful to glass electrodes, such as those used in transcutaneous measurement, and they disadvantageously change the sensor properties with respect to sensitivity and response time. Before a $CO_2$ measurement can be made with the known sensor, the sensor is calibrated using a known $CO_2$ concentration. To this end, the sensor is exposed to a gas mixture of carbon dioxide and air of a fixed composition. The partial pressures of water vapor and $CO_2$ of the calibration gas should agree with the corresponding partial pressures in the electrolyte, so that a diffusion of water vapor and $CO_2$ out of the electrolyte is prevented.

This kind of calibration is tedious and expensive, however, because a separate calibrating unit must always be kept in readiness, and to maintain the gas concentrations once they have been set, the calibrating unit must be flushed with the calibrating gas. It is also more difficult to handle the $CO_2$ sensor because the $CO_2$ sensor must be taken out of the calibrating container before it can be taken to the measurement location when a measurement is to be performed.

SUMMARY OF THE INVENTION

It is an object of the invention to improve a method of the above type such that while maintaining the operating conditions for the sensor and without having to introduce the sensor into a medium containing the calibrating gas, the composition of the electrolyte is not varied substantially.

This object is attained by providing that the membrane of the sensor is covered with a gas-tight and water-vapor-tight overlay, and that the isotonic equilibrium is brought about and maintained by means of the gas diffusing out of the electrolyte through the membrane and as far as the overlay.

It is thereby possible to keep the gas sensor in a condition of readiness during intervals between measurements or during relatively long storage while maintaining its operating conditions; while the sensor is in this condition of readiness, the composition of the electrolyte varies only insignificantly, despite an elevated operating temperature, and so within a prescribed calibration interval, a gas measurement can be done without requiring an additional calibration, or without requiring that a startup time elapse between when the sensor is started after some time out of operation and when it is ready for use. Under these conditions, all that needs to be done is to remove the overlay from the sensor membrane; the sensor is then immediately ready for making measurements.

By using the method according to the invention, the electrolyte of the sensor is advantageously isolated from its surroundings, so that the extremely small-volume space between the overlay and the measuring electrode can become saturated, for instance with $CO_2$ and water vapor; as a result, the electrolyte is in an environment of isotonic equilibrium. The $CO_2$ dissolved in the electrolyte is sufficient to saturate this volume with $CO_2$, so that the space between the overlay and the measuring electrode can in a sense be considered a calibration volume. The temperatures of from 37° to 44° C. that are required for operating a sensor for transcutaneous determination of $CO_2$ are not deleterious to maintaining this equilibrium.

An overlay for performing the method comprises a lined aluminum foil having an adhesive layer, which has an opening that receives the membrane. Once a measurement has been done, the sensor is covered by sticking the overlay onto the periphery of the sensor by means of the adhesive layer; the membrane of the sensor is thereby covered in a water-vapor-tight and gas-tight manner. The aluminum foil prevents as blocking layer diffusion of water vapor and gas out of the electrolyte into the ambient atmosphere even at elevated operating temperature of for instance from 37 to 44° C. During the entire readiness period, the overlay remains on the sensor, and there are no restrictions on the length of the readiness period.

Polyethylene has been shown to be a favorable lining for the aluminum foil.

To improve handling, the adhesive layer can furthermore be provided, in a certain area, with a non-adhesive coating, which enables the user to remove the overlay from the sensor again in a simple manner, as soon as the readiness period is over.

The nonadhesive coating may preferably be of silicone or silicone-treated paper.

BRIEF DESCRIPTION OF THE DRAWING

The figure of the drawing is a side elevation view of a gas sensor equipped with an overlay according to an embodiment of the invention.

DESCRIPTION OF THE PREFERRED EMBODIMENTS OF THE INVENTION

In the drawing figure, a $CO_2$ sensor is shown which has an electrode arrangement 2 disposed in its measurement head 1. The electrode arrangement includes a glass electrode 3, in which a wire lead 4 is guided to a measurement line 5. The electrode arrangement 2 is closed off by a membrane 6 that is permeable to $CO_2$ and water vapor, and the electrolyte (not shown) is located between the membrane 6 and the electrode arrangement 2. On the side nearer the membrane 6, the measurement head 1 is closed off by the overlay 7, which is secured on the measurement head 1 with the annular adhesive layer 8, which has an opening 13. The aluminum foil 9 is provided with a lining 14 which can be made of polyethylene. The aluminum foil 9 forms that part of the overlay 7 that is impermeable to $CO_2$ and water vapor and a nonadhesive coating 10 is applied to the free, protruding portion 12 of the layer 15 conjointly defined by the aluminum foil 9 and the lining 14.

After the overlay 7 is applied to the measurement head 1, the intermediate space 11 formed between the overlay 7 and the membrane 6 becomes saturated with water vapor and $CO_2$ from the electrolyte, so that an equilibrium of the partial pressures of water vapor and $CO_2$ prevails between the electrolyte and the intermediate space 11; as a result, the composition of the electrolyte does not vary further during the readiness period.

It is understood that the foregoing description is that of the preferred embodiments of the invention and that various changes and modifications may be made thereto without departing from the spirit and scope of the invention as defined in the appended claims.

What is claimed is:

1. An overlay for use in a method for conditioning a gas sensor such as for measuring the $CO_2$ partial pressure, the gas sensor having an electrode arrangement surrounded by an electrolyte and a gas-permeable membrane for partitioning off the electrode arrangement from the atmosphere, the method including the steps of covering the membrane of the sensor with a gas-tight and a water-vapor-tight overlay; and, generating and maintaining an isotonic equilibrium by means of the gas diffusing from the electrolyte through the membrane to the overlay; the overlay comprising:

an aluminum foil;

a lining formed on said aluminum foil so as to conjointly define a layer therewith; and, an adhesive coating formed on said layer and defining an opening adapted to be directly above said membrane when attached to the gas sensor.

2. The overlay of claim 1, said lining being made of polyethylene.

3. The overlay of claim 1, said adhesive coating defining a region provided with a non-adhesive coating.

4. The overlay of claim 3, said non-adhesive coating containing silicone.

* * * * *